United States Patent [19]

Mrozik et al.

[11] 4,289,760
[45] Sep. 15, 1981

[54] 23-KETO DERIVATIVES OF C-076 COMPOUNDS

[75] Inventors: Helmut H. Mrozik, Matawan; John G. MacConnell, Westfield, both of N.J.; August J. Kempf, Staten Island, N.Y.

[73] Assignee: Merck & Co., Inc., Rahway, N.J.

[21] Appl. No.: 146,725

[22] Filed: May 2, 1980

[51] Int. Cl.$^3$ .................. A61K 31/71; A61K 31/335; C07H 17/08; C07D 313/00
[52] U.S. Cl. .................................... 424/181; 424/279; 536/17 A; 260/343.41; 435/119
[58] Field of Search ................. 260/343.41; 536/17 R, 536/17 C; 424/181, 279

[56] References Cited

U.S. PATENT DOCUMENTS

| | | | |
|---|---|---|---|
| 4,156,720 | 5/1979 | Fisher et al. | 536/17 R |
| 4,171,314 | 10/1979 | Chabala et al. | 536/17 R |
| 4,172,940 | 10/1979 | Chaiet | 536/17 R |
| 4,199,569 | 4/1980 | Chabala et al. | 536/17 C |
| 4,200,581 | 4/1980 | Fisher et al. | 536/17 C |
| 4,201,861 | 5/1980 | Mrozik et al. | 536/17 C |
| 4,203,976 | 5/1980 | Fisher et al. | 536/17 C |
| 4,206,205 | 6/1980 | Mrozik et al. | 536/17 C |

FOREIGN PATENT DOCUMENTS 77-2345 of 0000 South Africa .................... 536/17 A Primary Examiner—Henry Jiles
Assistant Examiner—Jane T. Fan
Attorney, Agent, or Firm—David L. Rose; Harry E. Westlake

[57] ABSTRACT

Derivatives of C-076 compounds are described in which the C-076 molecule, a series of macrolides, has the 23-hydroxy group thereof oxidized to the 23-keto group. The 23-keto compounds are prepared by selectively oxidizing the suitably protected 23-hydroxy compound using such oxidizing agents as pyridinium dichromate, chromic acid-dimethyl pyrazole, chromic acid, chromic acid-acetic acid, and the like. Alternatively, selective oxidation of the unprotected 23-hydroxy compound may be accomplished by placing the compound in soil. Further reaction of the oxidized C-076 compounds is also possible. The compounds thus produced have profound anthelmintic, insecticidal, ectoparasiticidal, and acaricidal activity. Compositions containing the described C-076 derivatives as the active ingredient thereof are also disclosed.

6 Claims, No Drawings

23-KETO DERIVATIVES OF C-076 COMPOUNDS

BACKGROUND OF THE INVENTION

The term C-076 is used to describe a series of compounds isolated from the fermentation broth of a C-076 producing strain of *Streptomyces avermitilis*. The morphological characteristics of the culture are completely described in U.S. application Ser. No. 772,601, which is published as a German patent publication No. P27,170,407. The C-076 compounds are a series of macrolides each of which is substituted thereon at the 13-position with a 4-(α-L-oleandrosyl)-α-L-oleandrose group. The 2-series of C-076 compounds also has a 23-hydroxy group as well as several other hydroxy groups. The selective oxidation of the 23-hydroxy group, without affecting the remaining hydroxy groups is the subject matter of the instant application. The C-076 compounds and the instant derivatives thereof have a very high degree of anthelmintic and antiparasitic activity.

SUMMARY OF THE INVENTION

The C-076 series of compounds have the following structural formula:

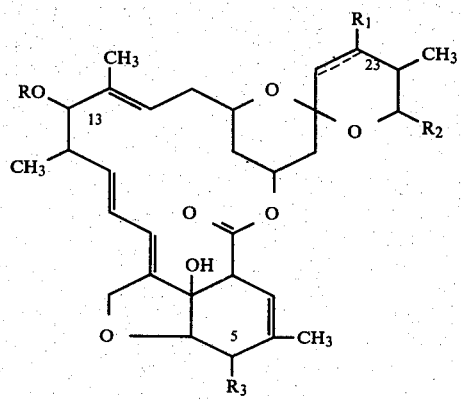

wherein R is the 4'-(α-oleandrosyl)-α-L-oleandrose group of the structure:

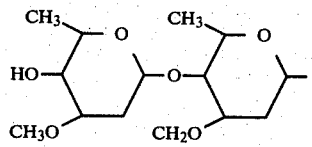

and wherein the broken line indicates a single or a double bond; $R_1$ is hydroxy and is present only when said broken line indicates a single bond;

$R_2$ is iso-propyl or sec-butyl; and $R_3$ is methoxy or hydroxy.

There are eight different C-076 compounds and they are given the designations A1a, A1b, A2a, A2b, B1a, B1b, B2a and B2b based upon the structure of the individual compounds.

In the foregoing structural formula, the individual C-076 compounds are set forth below:

| Compound | $R_1$ | $R_2$ | $R_3$ |
|---|---|---|---|
| A1a | Double bond | sec-butyl | —OCH$_3$ |
| A1b | Double bond | iso-propyl | —OCH$_3$ |
| A2a | —OH | sec-butyl | —OCH$_3$ |
| A2b | —OH | iso-propyl | —OCH$_3$ |
| B1a | Double bond | sec-butyl | —OH |
| B1b | Double bond | iso-propyl | —OH |
| B2a | —OH | sec-butyl | —OH |
| B2b | —OH | iso-propyl | —OH |

The C-076 compounds wherein the broken line indicates a single bond and $R_1$ is hydroxy are identified as the "2-series" since all such compounds are identified with a 2 in the name. The compounds of the instant invention are formed when the 23-hydroxy group ($R_1$) is oxidized to a ketone. In addition, either before or after the oxidation of the 23-hydroxy group, other derivatives of the molecule may be prepared, such as the removal of one or both of the α-L-oleandrose moieties, acylation of one or more of the hydroxy groups and the like.

Thus, it is an object of this invention to provide for novel 23-ketone compounds. It is a further object to describe processes for the preparation of such compounds. A still further object is to describe the use of such compounds as antiparasitic agents and to provide for compositions for such uses. Further objects will become apparent upon reading the following description of the invention.

DESCRIPTION OF THE INVENTION

The compounds of the instant invention are best described by the following structural formula:

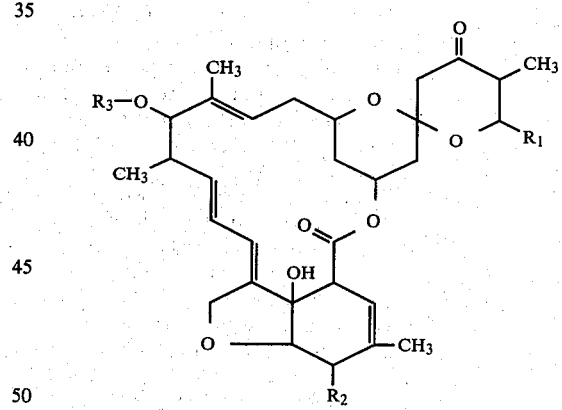

wherein $R_1$ is iso-propyl or sec-butyl;

$R_2$ is methoxy, hydroxy, lower alkanoyloxy or substituted lower alkanoyloxy wherein the substituent is hydroxy, carboxy, phenoxy or mono-, di- or tri- halo such as trifluoroacetyl, trichloroacetyl, chloroacetyl and the like; and $R_3$ is hydrogen, α-L-oleandrosyl, 4'-(α-L-oleandrosyl)-α-L-oleandrosyl, 4"-lower alkanoyl-4'-(α-L-oleandrosyl)-α-L-oleandrosyl, or 4"(substituted lower alkanoyl)-4'-(α-L-oleandrosyl)-α-L-oleandrosyl wherein the substituent is hydroxy, carboxy, phenoxy or mono-, di-, or tri-halo such as trifluoroacetyl, trichloroacetyl, chloroacetyl and the like.

In the instant invention, the term "lower alkanoyl" or "lower alkanoyloxy" is intended to include those lower alkanoyl groups and the lower alkanoyl portion of the lower alkanoyloxy groups which contain from 2–6 carbon atoms. Exemplary of such groups are acetyl, propionyl, butyryl, pivaloyl, and the like.

The term "halo" or "halogen" is intended to include the halogens fluorine, chlorine, bromine or iodine.

Preferred compounds of the instant invention are realized when:

$R_1$ is iso-propyl or sec-butyl;

$R_2$ is methoxy, hydroxy or lower alkanoyloxy; and $R_3$ is 4"-(α-L-oleandrosyl)-α-L-oleandrosyl, or 4"-lower alkanoyl-4'-(α-L-oleandrosyl)-α-L-oleandrosyl.

Further preferred compounds are realized when:

$R_1$ is iso-propyl or sec-butyl;

$R_2$ is methoxy, hydroxy or acetyl; and $R_3$ is 4'-(α-L-oleandrosyl)-α-L-oleandrosyl or 4"-acetyl-4'-(α-L-oleandrosyl)-α-L-oleandrosyl.

As is readily apparent from an examination of the C-076 molecule, there are at least two (for the A compounds) and sometimes three (for the B compounds) hydroxy groups present in addition to the 23-hydroxy, which are to be oxidized to prepare the compounds of the instant invention. Thus, an object of this invention is to oxidize the 23-hydroxy group, and leave the other hydroxy groups intact. This could be done by using a procedure which is selective for the 23-hydroxy or protecting the hydroxy groups which are not to be oxidized.

The procedure for selectively oxidizing the 23-hydroxy group to the 23-keto group is carried out by placing the unprotected C-076 starting material, preferably C-076 B2a, in soil at a rate of from 100 micrograms to 10 grams per liter of soil. Normal non-sterilized agricultural soil is utilized at ambient growing temperatures. Generally, an acetone solution of the C-076 starting material is sprayed over the soil wherein the conversion is to take place. Once the 23-keto compound is formed in the soil, plants growing in such soil are protected from nematode damage by such 23-keto compound formed in situ in the soil. In these cases, the 23-hydroxy compound is applied to the soil at a rate of from 20 micrograms to 20 milligrams per liter of soil, in order to result in the correct amount of 23-keto compound present in soil. However, it is also possible to extract the 23-keto compound from the soil after its formation. In this case, larger amounts of the 23-hydroxy compound may be applied to the soil; from 100 milligrams to 10 g of the 23-hydroxy compound per liter of soil. The conversion to the 23-keto compound takes place in from 2 to 20 days and the compound is removed from the soil, if desired, by extraction with an organic solvent such as ketone, preferably acetone, or a lower alkanol, preferably methanol or ethanol. It has been found that most of the 23-keto compound is produced during the 7th to the 10th day in the soil and may successfully be extracted from the soil at that time. When the 23-keto compound is to be extracted from the soil for other uses or further reaction, the soil temperature is best maintained at from 20° to 30° C.

Once the 23-keto compound is removed from the soil by extraction, it is purified using known techniques such as column, thin layer, high pressure liquid chromatography and the like. Once purified, the 23-keto compound may be employed for antiparasitic uses or it may be further reacted, as described below, to produce other derivatives of 23-keto C-076 compounds.

The 23-keto compounds may also be prepared chemically from the 23-hydroxy compounds using chemical oxidation techniques and protection of the other reactive hydroxy groups at the 4",5, and 13-positions. The 7-hydroxy group, being a tertiary hydroxy group is not susceptible to oxidation.

In the following description of the preparation of protected C-076 compounds, it is noted that such protected compounds with the 23-keto group are novel compounds and such compounds also have considerable antiparasitic activity. These protected derivatives are included within the ambit of the instant invention.

The preferred protecting group for the 4" and 5 positions is a trisubstituted silyloxy acetyl group. The most preferred group is the tert-butyldimethylsilyloxy acetyl group. The 4"-protected C-076 A2a/A2b and the 4",5-diprotected C-076 B2a/B2b compounds are prepared by combining the C-076 unprotected compound in an aprotic solvent such as methylene chloride, toluene, benzene, ethyl acetate, tetrahydrofuran and the like and adding the protecting reagent which is the acid halide of the protecting group. The preferred reagent is tert-butyl-dimethylsilyloxy acetyl chloride. Also, in order to minimize side reactions, there is included in the reaction mixture a tertiary amine to react with the acid halide released during the course of the reaction. Preferred amines are pyridine and triethylamine. The tertiary amine is required in amounts equimolar to the amount of acid halide liberated; however, generally several equivalents of the amine are employed. It is even possible to dispense with the solvent and use the amine in such excess that such amine, in effect, becomes the solvent. The reaction is stirred at from 0° C. to the reflux temperature of the reaction mixture and is complete in from ½ to 16 hours.

The protected compounds having the trisubstituted silyloxy acetyl protecting group at the 4"- and 5-positions have such protecting groups removed in two steps. In the first step the protected compound is stirred at room temperature in a lower alkanol such as methanol, for about 30 minutes in the presence of p-toluene sulfonic acid. A single molar equivalent of p-toluene sulfonic acid is employed.

The product from this reaction has at the 4"- or 5-positions the hydroxy acetoxy group. That is, the tert-butyl dimethyl silyl group has been removed. Thus, the first step for the removal of the protecting group is also a method for preparing the hydroxy acetoxy compounds of this invention. Following this, the protected intermediate is treated with sodium methoxide in methanol at room temperature for from ½ to 2 hours. The hydroxy acetyl group is cleaved, leaving the hydroxy group, which product is isolated using techniques known to those skilled in this art.

Alternatively, the trisubstituted silyloxy acetyl protecting group may be removed in one step. Treatment with sodium methoxide at about room temperature for up to 6 hours will generally afford the desired unprotected product.

Other useful protecting groups and derivatives of 23-hydroxy starting materials and 23-keto products are acyl and substituted acyl, particularly lower alkanoyl and substituted lower alkanoyl such as acetyl, trifloroacetyl, trichloroacetyl, chloroacetyl, hydroxyacetyl, carboxy acetyl, phenoxyacetyl, and the like. Such acylated compounds are prepared using such acylating reagents as the halide, preferably the chloride, of the acyl group being substituted on the substrate. Additional reagents such as the anhydride or haloformate are also useful.

In those reactions employing a halide reagent, it is advantageous to include in the reaction mixture a basic compound capable of reacting with and neutralizing the hydrogen halide liberated during the course of the reaction. Tertiary amines are preferred such as triethylamine, pyridine, dimethylamino pyridine, diisopropyl ethylamine, and the like. The basic compound is required in equimolar amounts relative to the moles of hydrogen halide liberated, however, excess amounts, even using the basic compound as a solvent, are not detrimental.

The starting materials are acylated in a solvent, preferably pyridine, at from 0° C. to room temperature, preferably room temperature, and the reactions are complete in from 4–24 hours. The products are isolated using known techniques.

The acyl protecting groups are readily removed by hydrolysis of the protected compound catalyzed with a mild base in a lower alkanol at from 0° C. to room temperature; the reaction is complete in from 1–24 hours.

The 23-hydroxy group is oxidized to the 23-keto group using oxidizing agents such as pyridinium dichromate; oxalylchloride-dimethylsulfoxide; acetic anhydride-dimethylsulfoxide; chromic acid-dimethylpyrazole; chromic acid; trifluoromethylacetic anhydridedimethylsulfoxide; m-chlorosuccinimidate chromic acid-acetic acid; and the like. Oxalylchloride-dimethylsulfoxide is the preferred oxidizing agent. Suitably protected compounds, as described above, are employed. The reaction is carried out at from dry-ice bath temperatures to room temperature, preferably from dry-ice bath temperatures to 0° C. and is complete in from 1–24 hours. The reaction may be carried out in any solvent in which the starting materials are reasonably soluble, and which will not react with the oxidizing agent. Such solvents as dimethylformamide, dimethylsulfoxide, methylene chloride, chloroform, carbon tetrachloride and the like are acceptable. For pyridinium dichromate reactions, dimethylformamide and dimethylsulfoxide are preferred. For chromic acid-dimethylpyrazole reactions, methylene chloride is preferred. The compounds are isolated from the reaction mixture using procedures known to those skilled in the art.

The carbohydrate side chain at the 13-position of the parent C-076 compounds is the 4'-(α-L-oleandrosyl)-α-L-oleandrose group and procedures for the selective removal of one or both of the sugar moieties to prepare the C-076 monosaccharide and C-076 aglycone respectively are available.

The reaction conditions which are generally applicable to the preparation of both the monosaccharide and aglycone involve dissolving the C-076 compound in an aqueous non-nucleophilic organic solvent-miscible with water, preferably dioxane, tetrahydrofuran, dimethoxyethane, dimethyl formamide, bis-2-methoxyethyl ether and the like, in which the water concentration is from 0.1 to 20% by volume. Acid is added to the aqueous organic solvent to the extent of 0.01 to 10% by volume. The reaction mixture is generally stirred at about 20°–40° C., preferably at room temperature, for from 6 to 24 hours. The lower concentrations of acid, from about 0.01 to 0.1% will predominately produce the monosaccharide under the above reaction conditions. Higher acid concentrations, from about 1 to 10% will predominantly produce the aglycone under the above reaction conditions. Intermediate acid concentrations will generally produce mixtures of monosaccharide and aglycone. The products are isolated and mixtures are separated by techniques such as column, thin layer, preparative layer and high pressure liquid chromatography, and other known techniques.

The acids which may be employed in the above process include mineral acids and organic acids such as sulfuric, hydrohalic, phosphoric, trifluoroacetic, trifluoromethanesulfonic and the like. The hydrohalic acids are preferably hydrochloric or hydrobromic. The preferred acid in the above process is sulfuric acid.

A further procedure for the preparation of the monosaccharide uses 1% sulfuric acid by volume in isopropanol at from 20°–40° C., preferably room temperature, for from 6 to 24 hours. For the preparation of the aglycone, 1% sulfuric acid, by volume, in methanol under the foregoing reaction conditions has been found to be appropriate.

The other acids listed above may also be employed for this process, at approximately the concentration employed for sulfuric acid.

The above described monosaccharide and aglycone compounds are isolated from the reaction mixture and mixtures of compounds are separated using techniques known to those skilled in this art, in particular the chromatographic techniques described above.

It is apparent that upon the removal of one or both glycosyl groups, there remain hydroxy groups at the 4'-(for the monosaccharide) and at the 13-(for the aglycone) positions. These hydroxy groups are about as reactive as the 4'' and 5-position hydroxy groups, and the acyl derivatives which may be substituted at such 4'' and 5-positions may also be substituted at these 4' and 13-positions. The reaction conditions described above are equally applicable to such compounds.

The novel compounds of this invention have significant parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesphagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia, and Oesphagostomum attack primarily the intestinal tract while others, such as Haemonchus and Ostertagia, are most prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The 23-keto C-076 compounds of this invention have unexpectedly high activity against these parasites, and in addition are also active against Dirofilaria in dogs, Nematospiroides, Syphacia, Aspiculuris in rodents, arthropod ectoparasites of animals and birds such as ticks, mites, lice, fleas, blowfly, in sheep Lucilia sp., biting insects and such migrating dipterous larvae as Hypoderma sp., in cattle, Gastrophilus in horses, and Cuterebra sp., in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra-intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blattella sp., clothes moth, Tineola sp., carpet beetle, Attagenus sp., and the housefly Musca domestica.

The compounds are also useful against insect pests of stored grains such as Tribolium sp., Tenebrio sp., and of agricultural plants such as spider mites, (Tetranychus sp.), aphids, (Acyrthiosiphon sp.), against migratory orthopterans such as locusts and immature stages of insects living on plant tissue. The compounds are useful as a nematicide for the control of soil nematodes and plant parasites such as Meloidogyne sp., which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the C-076 derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of hose animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparations using solketal, glycerol formal, and aqueous parenteral formulations are also used. The active monosaccharide or aglycone C-076 compound or compounds are dissolved or suspended in the parenteral formulation for administration; such formulations generally contain from 0.005 to 5% by weight of the active compound.

Although the antiparasitic agents of this invention find their primary uses in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg. per kg. of animal body weight, such total dose being given at one time or in divided doses over a relatively short period of time such as 1-5 days. With the preferred compounds of the invention, excellent control of such parasites is obtained in animals by administering from about 0.025 to 0.5 mg. per kg. of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active 23-keto C-076 compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular C-076 derivative employed, the compounds of this invention are usually fed at concentrations of between 0.00001 to 0.002% in the feed in order to achieve the desired antiparasitic result.

In using the compounds of this invention, the individual 23-keto C-076 components may be prepared and used in that form. Alternatively, mixtures of two or more of the individual 23-keto C-076 components may be used, as well as mixtures of the parent C-076 compounds other C-076 compounds or other active compounds not related to C-076 and the compounds of this invention.

In the isolation of the C-076 compounds, which serve as starting materials for the instant processes, from the fermentation broth, the various C-076 compounds will be found to have been prepared in unequal amounts. In particular an "a" series compound will be prepared in a higher proportion than the corresponding "b" series compound. The weight ratio of "a" series to the corresponding "b" series is about 75:25 to 99:1. The differences between the "a" series and "b" series is constant throughout the C-076 compounds and consists of a sec-butyl group and an iso-propyl group respectively at the 25-position. This difference, of course, does not interfere with any of the instant reactions. In particular, it may not be necessary to separate the "b" components from the related "a" component. Separation of these closely related compounds is generally not practiced since the "b" compound is present only in a very small percent by weight, and the structural difference has negligible effect on the reaction processes and biological activities.

In particular, it has been found that the starting materials for the compounds of this invention are very often prepared in a ratio of about 80% C-076 B1a or A1a and 20% C-076 B1b or A1b. Thus, the preferred composition of this invention is one which contains about 80% of the "a" component and 20% of the "b" component.

The C-076 compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

The following examples are provided in order that this invention might be more fully understood; they are not to be construed as limitative of the invention.

The 23-keto C-076 derivatives prepared in the following examples are generally isolated as amorphous solids and not as crystalline solids. They are thus characterized analytically using techniques such as mass spectrometry, nuclear magnetic resonance, and the like. Being amorphous, the compounds are not characterized by sharp melting points; however, the chromatographic and analytical methods employed indicate that the compounds are pure.

EXAMPLE 1

23-Keto-C-076B2a

A. 4″,5-Di-O-(tert-butyl-dimethylsilyloxyacetyl)C-076 B2a

In a flame dried reaction vessel containing dry nitrogen are combined 2.0 gm. of C-076 B2a, 25 ml. of diethyl ether and 2.5 ml. of dry pyridine. The solution is cooled to 0° C. in an ice bath and 8 ml. of a diethyl ether solution containing 940 mg. of tert-butyl dimethylsilyloxyacetyl chloride is added along with 600 mg. of tert-butyl dimethylsilyl chloride. The addition produces a white precipitate. The reaction mixture is stirred for 30 minutes in an ice bath after which thin layer chromatographic analysis indicates that the reaction is not yet complete. An additional 8 ml. of an ether solution containing 100 mg. of tert-butyl dimethylsilyloxyacetyl chloride per ml. of solution is added and the reaction mixture stirred for an additional 80 minutes. Thin layer chromatographic analysis indicates the absence of starting material in the reaction mixture. 200 Ml. of cold water is added to the reaction mixture which is then extracted 5 times with 100 ml. portions of diethyl ether. The combined ether extracts are washed 7 times with 20 ml. portions of water and once with a 1:1 mixture of water and aqueous saturated sodium chloride. The ether layer is dried over magnesium sulfate and evaporated to dryness in vacuo. The residue is combined twice with diethyl ether, once with toluene and once again with diethyl ether and dried under high vacuum affording 3.2 g. of a clear white foam which is purified on a column of 175 g. of silica gel eluting with 15% ethyl acetate in methylene chloride. The first 500 ml. of eluant is discarded and 20 ml. fractions are collected thereafter. Fractions 39–63 are collected affording 1.34 g. of a white foam which is indicated by mass spectrometry, and 300 mHz nuclear magnetic resonance to be 4″-5-di-O-(tert-butyl-dimethylsilyloxyacetyl) C-076 B2a.

B.

4″,5-Di-O-(tert-butyl-dimethylsilyloxyacetyl)-23-keto-C-076 B2a 12.4 Mg. (0.01 mmoles) is dissolved in 0.5 ml. of dry dimethylformamide and 37.6 mg. (0.1 mmoles) of pyridinium dichromate is added in one portion with stirring at room temperature. The reaction mixture is stirred at room temperature for 3½ hours. An aliquot is removed and analyzed on a thin layer chromatography silica gel plate and shows no starting material. The reaction is diluted with 5 ml. of ice water and extracted three times with ether. The ether extracts are washed twice with water and once with saturated sodium chloride. After drying with magnesium sulfate and evaporation to dryness in vacuo, there is recovered 10.5 mg. of a white foam. The foam is purified on a preparative layer chromatography plate with 250μ of silica gel and eluted with 5% tetrahydrofuran and 0.15% ethanol in methylene chloride. The product band is removed from the plate using 25% ethyl acette in methylene chloride, filtered and evaporated to dryness affording 7.0 mg. of a white glass which is identified with mass spectrometry and 300 MHz nuclear magnetic resonance as 4″,5-di-O-(tert-butyl-dimethylsilyloxyacetyl)-23-keto-C-076 B2a.

C. 4″,5-Di-(O-hydroxyacetyl)-23-keto C-076 B2a 4.6 Mg. (0.0037 mmoles) of 4″,5-di-O-(tert-butyldimethylsilyloxyacetyl)-23-keto-C-076 B2a is dissolved in 1.38 ml. of 1% p-toluenesulfonic acid in methanol and stirred at room temperature for 55 minutes. The reaction mixture is diluted with 5 ml. of dilute sodium bicarbonate (prepared from 0.5 ml. of saturated sodium bicarbonate and 4.5 ml. of water) and extracted three times with ether. The ether is washed three times with water, once with saturated sodium chloride, dried and evaporated to dryness in vacuo affording 4.8 mg. of a yellow foam which is used without further purification in the next step.

D. 23-Keto-C-076 B2a 4.8 Mg. (0.0048 mmoles) of the product from Example 1 part C is dissolved in 0.5 ml. of dry methanol and 39 μl (0.0048 mmoles) of a sodium methoxide in methanol solution (prepared from 28 mg. of sodium and 10 ml. of dry methanol). The reaction is stirred at room temperature for 90 minutes. The reaction mixture is diluted with 5 ml. of water containing 1 drop of acetic acid and extracted three times with ether. The ether extracts are washed three times with water, once with dilute sodium bicarbonate, once with saturated sodium chloride solution, dried over magnesium sulfate and evaporated in a stream of nitrogen. The residue is dried under high vacuum affording 2.9 mg. of a glassy residue. The residue is purified on a preparative layer chromatography plate coated with 250μ of silica gel, eluting with 5% methanol in chloroform. The bands containing product are located under ultraviolet light and removed from the silica gel with ethyl acetate. Three bands are isolated on the plate and the middle band is 23-keto-C-076 B2a as determined by 300 MHz nuclear magnetic resonance. 1.5 Mg. are isolated.

EXAMPLE 2

4″,5-Di-O-phenoxyacetyl C-076 B2a/B2b

1 G. of C-1076 B2a/B2b is dissolved in 10 ml. of methylene choride which contains 0.25 ml. of pyridine. The solution is placed under nitrogen and cooled in an ice bath. With stirring, 10 ml. of methylene chloride containing 0.39 ml. of phenoxyacetylchloride is added, and the mixture stirred for 1 hour in an ice bath. The reaction mixture is poured onto 100 ml. of ice water and extracted 3 times with ether. The combined ether extracts are washed 3 times with water, once with saturated sodium chloride, dried over magnesium sulfate, and evaporated to dryness in vacuo. The residue is chromatographed on 80 g. of silica gel eluting with 12% ethyl acetate in methylene chloride. Fractions 1-10 are discarded; fractions 11-20 afford 49 mg. of a pale yellow film; and fractions 25-72 afford 880 mg. of a white foam which is identified by 300 mHz nuclear magnetic resonance as 4″,5-di-O-phenoxyacetyl C-076 B2a/B2b.

EXAMPLE 3

23-Keto-C-076 B2a

1200 Ml. of soil mixture consisting of 60% loam and 40% sand is treated with 6 mg. of C-076 B2a on 600 mg. of clay carrier. The soil mixture is allowed to stand for 13 days. The soil is then extracted with about 4 liters of acetone with stirring for about ½ hour. The acetone is filtered through prewashed diatomaceous earth on a sintered glass funnel. The filtrate is then concentrated to a volume of 200 ml. A sample of the concentrate is evaporated to dryness, combined with ethyl acetate and dried in high vacuum. The residue is taken up in methylene chloride and passed through a column of equal amounts of activated carbon and acid-washed alumina eluted with methylene chloride. The eluant is changed to 15% isopropanol in methylene chloride. The column eluate is evaporated to dryness and high pressure liquid chromatography in methanol of the residue afford 23-keto C-076 B2a as 44% of total solids recovered.

EXAMPLE 4

4″,5-Di-O-(Phenoxyacetyl)-23-keto-C-076 B2a

Into a solution of 55 ml. of methylene chloride is added 3.21 g. (2.21 ml., 25.2 mmoles) of oxalylchloride. The reaction mixture is cooled in a dry-ice/acetone bath under a stream of nitrogen and a mixture of 3.95 g. (3.6 ml., 50.5 mmoles) of dimethylsulfoxide in 20 ml. of methylene chloride is added over a period of 5 minutes. Bubbling is observed, and the mixture is stirred for 2 minutes. A solution of 13.3 g. (11.5 mmoles) of 4″,5-di-O-(phenoxyacetyl) C-076 B2a in 80 ml. of methylene chloride is added dropwise over 10 minutes, maintaining the temperature at −70° C. The reaction is at −60° to −50° C. for ½ hour and 16.1 ml. of triethylamine is then added over 5 minutes. The dry-ice bath is then removed and the reaction mixtures allowed to rise to room temperature over 45 minutes. The reaction mixture is poured into 500 ml. of ice water and the aqueous mixture extracted with 100 ml. followed three times with 75 ml. of ether. The combined ether layers are washed six times with 50 ml. of water, once with a saturated salt solution, and dried over magnesium sulfate. The aqueous layer is evaporated to dryness affording 12.9 g. of a light yellow solid material identified as 4″,5-di-O-(phenoxyacetyl)-23-keto-C-076 B2a.

Following the above procedure, using 4″-O-phenoxyacetyl C-076 A2a in place of 4″-5-di-O-(phenoxyacetyl)C-076 B2a, there is obtained 4″-O-phenoxyacetyl-23-keto-C-076 A2a.

EXAMPLE 5

23-Keto C-076 B2a

200 Ml. of methanol is cooled to 0° C. and ammonia gas is bubbled into it through an aerator for 1 hour to saturate the methanol. An additional 260 ml. of methanol is added followed by 12.9 g. of 4″,5-di-O-(phenoxyacetyl)-23-keto-C-076 B2a in 50 ml. of methanol. The reaction mixture is stirred at 0° C. for 45 minutes and at room temperature for 1 hour 15 minutes. The mixture is evaporated to dryness and ether is added to the residue. The ether solvent is evaporated in vacuo. Drying under high vacuum affords 13 g. of a yellow foam which is dissolved in 600 ml. of ether and washed 4 times with 50 ml. of water and once with saturated salt. The ether is dried over magnesium sulfate and evaporated to dryness affording 11.2 g. of a yellow foam. The foam is placed on a column of 500 g. of silica gel and eluted with 1:1 ethylacetate/methylene chloride mixture. The first 600 ml. of eluant is discarded and 20 ml. fractions taken thereafter. Fractions 1–91 are discarded. Fractions 92–120 are combined.

Following the above procedure, using 4″-O-phenoxyacetyl 23-keto C-076 A2a in place of 4″-5-di-O-(phenoxyacetyl) C-076 B2a, there is recovered 23-keto C-076 A2a, and concentrated in vacuo to 8.0 g. of a yellow foam. This is dissolved in about 60 ml. of ether and the phenoxy ammonium acetate allowed to crystallize. The solution is filtered, and the filtrate is concentrated affording 6.2 g. of a yellow foam which is identified as 23-keto C-076 B2a.

EXAMPLE 6

4″-O-(Chloroacetyl) C-076 A2a

100 Mg. of C-076 A2a is dissolved in 1.5 ml. dry pyridine, cooled in an ice bath and 300 mg. of chloroacetic anhydride is added maintaining the temperature at 0° C. The reaction mixture is worked up using lyophilization and preparative layer chromatography techniques as previously described affording 64 mg. of a white powder which nuclear magnetic resonance and mass spectrometry reveal to be 4"-O-(chloroacetyl) C-076 A2a.

EXAMPLE 7

4"-O-Chloroacetyl-23-keto-C-076-A2a

50 Mg. of 4"-O-chloroacetyl C-076 A2a is dissolved in 0.3 ml. of methylene chloride and added at −70° C. to a solution of an oxidant prepared at −70° C. from 9.6 μl. of oxalyldichloride and 16 μl. of dimethyl sulfoxide in 0.35 ml. of methylene chloride. The reaction mixture is stirred at −70° to −50° C. for 30 minutes, then 70 μl. of triethylamine is added. After an additional 5 minutes at low temperature, the reaction mixture is allowed to come to room temperature. The reaction mixture is added to water and purified by silica gel preparative layer chromatography to give 4"-O-chloroacetyl-23-keto-C-076-A2a, which is characterized by its MNR and mass spectra.

EXAMPLE 8

C-076 B2a 4",5-Di-O-Acetate

200 Mg. of C-076 B2a is dissolved in 3 ml. of dry pyridine and cooled in an ice bath. 1 Ml. of acetic anhydride is added and the reaction mixture is allowed to stand at 0° C. overnight. The reaction mixture is combined with benzene and lyophilized and the solid material purified by preparative layer chromatography on silica gel plates eluting with 5% tetrahydrofuran in chloroform affording 208 mg. of a white solid identified by mass spectrometry as C-076 B2a 4",5-di-O-acetate.

EXAMPLE 9

23-Keto-C-076-B2a-4",5-di-O-Acetate

A solution of 100 g. of C-076 B2a 4",5-di-O-acetate in 0.5 ml. of methylene chloride is added at −70° C. to a solution of oxidizing agents prepared at −70° C. from 20 μl. of oxalyl chloride and 32 μl. of dimethylformamide in 0.7 ml. of methylene chloride. The reaction mixture is kept at −70° to −50° C. for 30 minutes, then 0.15 ml. of triethylamine is added, and after 5 minutes at −50° to −70° C. the reaction mixture is allowed to warm up to room temperature. The mixture is poured onto ice water and extracted with methylene chloride and further purification by preparative layer chromatography on silica gel gives 23-keto-C-076-B2a-4",5-di-O-acetate, which is identified by its MNR and mass spectra.

EXAMPLE 10

23-Keto-C-076-B2a-Monosaccharide

500 Mg. of 23-keto-C-076-B2a is dissolved in 10 ml. of a solution of 0.1 ml. of concentrated sulfuric acid and 9.9 ml. of isopropanol. The reaction mixture is stirred at room temperature overnight. 125 Ml. of chloroform is added and the mixture washed once with 10 ml. of saturated sodium bicarbonate and once with 10 ml. of water. The organic layer is dried over magnesium sulfate and evaporated to dryness in vacuo affording a pale yellow solid material which is dissolved in chloroform and placed on 5 preparative layer chromatography silica gel plates and eluted twice with 2:1 benzene/ethylacetate. The slower moving major fraction contains a white powder after lyophilization from benzene which mass spectrometry and 300 MHz nuclear magnetic resonance indicates is 23-keto-C-076-B2a monosaccharide.

EXAMPLE 11

23-Keto-C-076-B2a-Aglycone

A solution of 100 mg. of 23-keto-C-076-B2a and 500 mg. of p-toluene sulfonic acid monohydrate in 10 ml. of methanol is kept 16 hours at room temperature, when thin layer chromatography shows that the reaction is complete. The mixture is added to 75 ml. of ether, washed with aqueous sodium bicarbonate solution and water and concentrated in vacuo. Further purification by silica gel preparative layer chromatography gives 23-keto-C-076-B2a-aglycone as the main product and some 23-keto-C-076-B2a monosaccharide as by-product both are identified by their MNR and mass spectra.

We claim:

1. A compound having the formula:

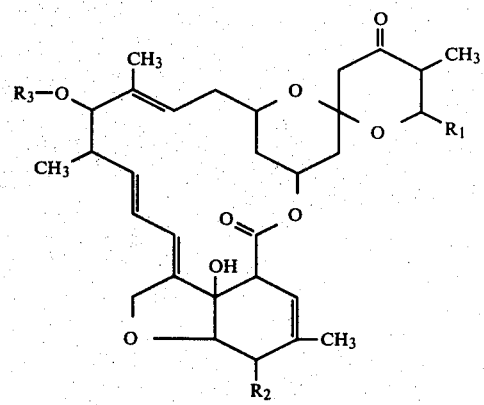

wherein $R_1$ is iso-propyl or sec-butyl;

$R_2$ is methoxy, hydroxy, lower alkanoyloxy or substituted lower alkanoyloxy wherein the substituent is hydroxy, phenoxy or mono-, di- or tri-halo; and $R_3$ is hydrogen, α-L-oleandrosyl, 4'-(α-L-oleandrosyl)-α-L-oleandrosyl, 4"-lower alkanoyl-4'-(α-L-oleandrosyl)-α-L-oleandrosyl, 4"-substituted lower alkanoyl)-4'-(α-L-oleandrosyl)-α-L-oleandrosyl wherein the substituent is hydroxy, carboxy, phenoxy or mono-, di- or tri-halo; and the 4"- and/or 5-trisubstituted silyloxyacetyl, acetyl, trifluoroacetyl, trichloroacetyl, chloroacetyl, hydroxyacetyl, carboxyacetyl, and phenoxyacetyl protected derivatives thereof.

2. The compound of claim 1 wherein:

$R_1$ is iso-propyl or sec-butyl;

$R_2$ is methoxy, hydroxy or lower alkanoyloxy; and $R_3$ is 4'-(α-L-oleandrosyl)-α-L-oleandrosyl or 4"-lower alkanoyl-4'-(α-L-oleandrosyl)-α-L-oleandrosyl.

3. The compound of claim 2 wherein:

$R_1$ is iso-propyl or sec-butyl;

$R_2$ is methoxy, hydroxy or acetyl; and $R_3$ is 4'-(α-L-oleandrosyl)-α-L-oleandrosyl or 4"-acetyl-4'-(α-L-oleandrosyl)-α-L-oleandrosyl.

4. The compound of claim 3 which is 23-keto C-076 B2a.

5. A method for the treatment of parasitic infections which comprises administering to an animal infected with parasites, an effective amount of a compound of claim 1.

6. A composition useful for the treatment of parasitic infections in animals which comprises an inert carrier and an effective amount of a compound of claim 1.

* * * * *